United States Patent

Rose-Fricker

[11] Patent Number: 6,066,786
[45] Date of Patent: May 23, 2000

[54] GLYPHOSATE TOLERANT FESCUE GRASSES

[75] Inventor: Crystal Rose-Fricker, Canby, Oreg.

[73] Assignee: Pure Seed Testing, Inc., Hubbard, Oreg.

[21] Appl. No.: 09/098,691

[22] Filed: Jun. 17, 1998

[51] Int. Cl.⁷ .............................. A01H 5/00; A01H 5/10; A01H 1/04
[52] U.S. Cl. ........................... 800/320; 800/298; 800/260
[58] Field of Search ..................... 800/298, 300, 800/320, 260; 435/172.1, 172.3

[56] References Cited

U.S. PATENT DOCUMENTS

| | | | |
|---|---|---|---|
| 4,757,011 | 7/1988 | Chaleff et al. | 435/172.1 |
| 4,761,373 | 8/1988 | Anderson et al. | 435/172.3 |
| 5,084,082 | 1/1992 | Sebastian | 71/90 |
| 5,188,642 | 2/1993 | Shah et al. | 800/235 |
| 5,304,732 | 4/1994 | Anderson et al. | 800/235 |
| 5,463,175 | 10/1995 | Barry et al. | 800/205 |
| 5,554,798 | 9/1996 | Lundquist et al. | 800/205 |
| 5,633,448 | 5/1997 | Lebrun et al. | 800/205 |
| 5,718,079 | 2/1998 | Anderson et al. | 47/58 |

OTHER PUBLICATIONS

*Field Day 15*, Turfgrass Breeding Progress, pp. 60–70, 1997. Published by Turf–Seed, Inc. and Pure Seed Testing, Inc.

*Field Day 14*, Turfgrass Breeding Progress, pp. 39–47 and 98–101, 1996. Published by Turf–Seed, Inc. and Pure Seed Testing, Inc.

*Primary Examiner*—Lynette R. F. Smith
*Assistant Examiner*—Melissa L Kimball
*Attorney, Agent, or Firm*—Klarquist Sparkman; Campbell Leigh & Whinston, LLP

[57] ABSTRACT

Glyphosate tolerant fescue (Festuca sp.) grasses are provided. These grasses are particularly suitable for use in lawns, golf courses and other turfs where weeds are a problem. Weed control in areas planted with the disclosed grasses can be achieved by direct application of glyphosate herbicides.

14 Claims, No Drawings

GLYPHOSATE TOLERANT FESCUE GRASSES

BACKGROUND OF THE INVENTION

Fescue Grasses

Fescue grasses (Festuca species) are widely used as turf in a variety of applications, including home lawns, golf courses, athletic fields, parks, pasture and along roadsides. Two types of fescue grasses are most commonly grown: tall fescues and fine fescues. Tall fescue grasses (such as *F. arundinacea*) have excellent drought and wear resistance. Tall fescue is adapted to a wide range of climactic conditions and is the most predominant cool-season, perennial grass in the United States. (See Tall Fescue, Edited by R. C. Buckner and L. P. Bush, Published by the American Society of Agronomy, Crop Science Society of America, and Soil Science Society of America. ASA Monograph Number 20. 1979. ISBN 0-89118-057-5). The term fine fescue encompasses several subtypes including hard fescue grasses (*F. longifolia*); these grasses are low maintenance and shade tolerant, but lack the durability of the tall fescue grasses.

Glyphosate Herbicides

Glyphosate (N-(phosphonomethyl) glycine) is the active ingredient in glyphosate herbicides, such as ROUNDUP® brand herbicide produced by Monsanto, St. Louis, Mo. Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® brand herbicide.

Glyphosate is a broad spectrum herbicide that inhibits the enzyme enolpyruvylshikimate-phosphate synthase (ESPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents have been issued that disclose various formulations of glyphosate, including U.S. Pat. Nos. 4,405,531; 5,118,338; 5,196,044; 5,639,711; 5,652,197; 5,679,621; and 5,750,468.

Little success has been reported in finding natural resistance to glyphosate herbicides in plants. This is beneficial in one respect since it indicates that the likelihood of glyphosate resistant populations of weeds arising is low, but it also means that no naturally resistant desirable plant species are available. As a result, great care must be taken when applying glyphosate herbicides in the vicinity of desirable plants (e.g., crops, ornamentals, grass turf). In order to increase the utility of glyphosate herbicides in crop species, a bacterial gene conferring glyphosate resistance has been introduced into a few crops, including soybean and corn (see U.S. Pat. Nos. 5,188,642; 5,463,175; 5,554,798; and 5,633,448). Weed growth in these transgenic crops may be controlled by application of glyphosate herbicides, without significantly adversely affecting the growth of the crop.

Glyphosate herbicides are highly effective against grass species, and so cannot be effectively applied to control weed growth in turf grasses. The production of transgenic grasses harboring a bacterial glyphosate resistance gene is hampered by the lack of reliable transformation procedures for grass species. It is also likely that public acceptance of transgenic grasses for widespread domestic use (for example, in home lawns) would be difficult.

SUMMARY OF THE INVENTION

The inventors have produced glyphosate tolerant fescue grasses capable of tolerating application of at least 1 pint per acre of agricultural grade formulations of glyphosate-based herbicides (such as ROUNDUP® brand herbicide produced by Monsanto, St. Louis, Mo.) (equivalent to application of approximately 0.056 g/square meter of the active ingredient, glyphosate). One of these grasses is a tall fescue, (*Festuca arundinacea*) that has been given experimental variety designation 5DU. The other is a hard fescue grass, (*Festuca longifolia*) experimental variety designated as 4RU. Use of these grasses as turf (for example in lawns, on golf courses and along roadsides) permits ready control of weeds by application of a glyphosate herbicide. Seed of 4RU and 5DU have been deposited with the ATCC.

In one embodiment, the invention provides fescue grass plants having the characteristic features of 4RU or 5DU, as well as seeds of such plants. In another embodiment, the invention provides grass plants having the genotype of 4RU or 5DU. The invention also encompasses fescue grass plants that are produced by crossing 4RU or 5DU with other grass varieties, as well as seeds of such plants. In another aspect, the invention provides a method of producing grass seed, comprising planting 4RU or 5DU grass seed under conditions that result in the germination of the seed, growth of grass plants and setting of progeny seed, and then harvesting the progeny seed. The invention also provides a method of producing a glyphosate-tolerant grass plant by crossing a first grass plant with one or more other grass plants to produce progeny grass plants, wherein the first grass plant is 4RU or 5DU, and then screening the progeny grass plants to select a progeny grass plant that is tolerant to glyphosate. Glyphosate-tolerant grass plant produced by this method are also encompassed by the invention.

These and other aspects of the invention will become more apparent from the following description.

DESCRIPTION OF THE INVENTION

Seed Deposits, Description of Plants

Seeds of 4RU were deposited with the American Type Culture Collection (ATCC, Manassas, Va.) on June 15, 1998, under accession number 209893. Seeds of 5DU were deposited with the American Type Culture Collection (ATCC, Manassas, Va.) on June 15, 1998, under accession number 209894. Both of these grasses are also maintained at, and available from, Pure Seed Testing, Inc., P.O Box 449, Hubbard, Oreg. 97032.

The following growth characteristics were observed for tall fescue grass 5DU plants that were approximately one year old, grown in seeded rows in the Willamette Valley of Oregon. Variations on these measurements may be observed for plants of differing ages, grown in other locations and/or under different prevailing weather conditions. (All length measurements are in cm unless otherwise indicated).

TABLE 1

Growth Characteristics of 5DU

| Characteristic | Mean | Std. D. | Std. Error | N | Min | Max. |
|---|---|---|---|---|---|---|
| Plant Height | 112.238 | 15.426 | 1.725 | 80 | 76.000 | 162.000 |
| Flag Leaf Height | 55.688 | 9.799 | 1.096 | 80 | 33.000 | 79.000 |
| Internode Length | 22.813 | 5.996 | 0.670 | 80 | 12.000 | 39.000 |
| Tiller Leaf Length | 19.175 | 4.517 | 0.505 | 80 | 12.000 | 37.000 |
| Tiller Leaf Width (mm) | 6.925 | 1.621 | 0.181 | 80 | 4.000 | 10.000 |
| Flag Leaf Length | 13.425 | 3.903 | 0.436 | 80 | 4.000 | 23.000 |
| Flag Leaf Width (mm) | 5.375 | 1.444 | 0.161 | 80 | 2.000 | 9.000 |

TABLE 1-continued

Growth Characteristics of 5DU

| Characteristic | Mean | Std. D. | Std. Error | N | Min | Max. |
|---|---|---|---|---|---|---|
| Panicle Length | 17.200 | 3.381 | 0.378 | 80 | 9.000 | 23.000 |
| Tiller Count (per 5 inches of of seeded row) | 70.875 | 18.828 | 6.656 | 8 | 39.000 | 93.000 |

The following growth characteristics were observed for hard fescue grass 4RU plants that were approximately two years old, grown as spaced plants in the Willamette Valley of Oregon. Variations on these measurements may be observed for plants of differing ages, grown in other locations and/or under different prevailing weather conditions. (All length measurements are in cm unless otherwise indicated).

TABLE 2

Growth Characteristics of 4RU

| Characteristic | Measurement | Standard Error |
|---|---|---|
| Plant Height | 74.18 | 1.14 |
| Bottom Tiller Leaf Length | 8.31 | 0.38 |
| Bottom Tiller Leaf Width (mm) | 1.38 | 0.06 |
| Top Flag Leaf Height | 27.48 | 0.67 |
| Panicle Length | 10.43 | 0.24 |
| Awn Length (minimum) (mm) | 1.4 | 0.08 |

Glyphosate Tolerance Characteristics

4RU and 5DU plants are tolerant to glyphosate herbicide applied at levels and/or frequency sufficient to remove weed species from lawns, pasture, golf courses, etc. As used herein the phrase "a glyphosate tolerant grass plant" is a grass plant that will survive application of agricultural formulations of glyphosate herbicide (containing 41% w/v glyphosate) at levels equivalent to at least 1 pint per acre, corresponding to at least about 0.056 g per square meter of active ingredient glyphosate. This level of glyphosate is sufficient to kill most common weeds. At the application rate of 1 pint per acre and under the field conditions prevailing at the time that the inventors performed the field tests on 4RU and 5DU (December through May in the Willamette Valley of Oregon), little or no yellowing of the grass was seen, and no substantial reduction in growth rate was detected. However, it is emphasized that more significant deleterious effects may be observed depending on the age of the grass, the time of year and the prevailing weather conditions. 4RU and 5DU will also tolerate at least 3 applications of this level of glyphosate herbicide at 6 week intervals, where necessary to remove weeds that are difficult to control.

Higher levels of glyphosate herbicide may also be applied to 4RU and 5DU plants if necessary to eradicate particularly recalcitrant weed species. 4RU and 5DU may tolerate application of at least 1 quart per acre of agricultural formulations of glyphosate herbicide (equivalent to about 0.112 g per square meter of active ingredient glyphosate) depending on the time of year, age of the plants and environmental conditions. At this level of glyphosate application, a substantial amount of yellowing and a substantial retardation of plant growth may be observed, but a high percentage of the grass plants are not killed and subsequently make a complete recovery.

The following tables show examples of field trials in which the glyphosate resistance characteristics of 4RU and 5DU were examined and compared to currently used hard and tall fescue grass varieties, respectively. Table 3 shows comparisons of the turf quality of 4RU with other hard fescue varieties in the absence of glyphosate herbicide and the damage to the grasses produced by application of a commercial formulation of glyphosate sprayed at the rate of 1 pint per acre. The score ratings are based on a scale of 1 to 9, typical of rating scales for turf grasses. For herbicide damage: 9=no damage; 8–7=10–20% yellowing; 6–5= 30–40% yellowing with minor growth retardation; 4–3= 50–60% yellowing with growth retardation; 2–1=70–90% yellowing with dead turf. For turf quality: 9=best turf quality, 0=dead turf Table 4 shows an equivalent comparison for 5DU and other tall fescue varieties. These tables show that 4RU and 5DU were significantly more tolerant of glyphosate herbicide than currently available hard and tall fescue varieties, while having at least as good turf quality.

TABLE 3

| Variety | Turf quality (no herbicide) | T group | Herbicide damage | T group |
|---|---|---|---|---|
| 4RU | 6.5 | A | 7 | A |
| Aurora | 6.5 | A | 4.5 | B |
| Discovery | 6 | A | 4.0 | B |

TABLE 4

| Variety | Turf quality (no herbicide) | T group | Herbicide damage | T group |
|---|---|---|---|---|
| 5DU | 8 | A | 6.67 | A |
| Coronado | 7.3 | AB | 4 | B |
| Apache II | 6.67 | B | 4 | B |
| Tomahawk | 6.67 | B | 3 | B |

Tables 5 and 6 show the effect of applying glyphosate herbicide at levels of 0.5 pints, 1 pint and 1 quart per acre to 4RU and 5DU grasses. The effect of the herbicide application on grass quality and on weed control is shown, using a scale of 0 to 9. A score of zero for herbicide damage indicates that the herbicide had no adverse effect on the grass, while a score of 9 indicates that the herbicide killed the grass. A score of 0 for weed control indicates no weed control, 9 represents complete weed control. These tables indicate that 4RU and 5DU tolerated levels of glyphosate at which most weed species were killed.

TABLE 5

| Herbicide applied to 4RU | Herbicide damage rated on indicated number of days post herbicide application | | | | Weed control rated on indicated number of days post herbicide application | | | |
|---|---|---|---|---|---|---|---|---|
| (rate per acre) | 20 days | 68 days | 103 days | 125 days | 20 days | 68 days | 103 days | 125 days |
| 0.5 pints | 0 | 0 | 0 | 1 | 0 | 7 | 9 | 9 |
| 1 pint | 0 | 2 | 2 | 2 | 0 | 9 | 9 | 9 |
| 1 quart | 0 | 4 | 3 | 3 | 0 | 9 | 9 | 9 |

TABLE 6

| Herbicide applied to 5DU | Herbicide damage rated on indicated number of days post herbicide application | | | | Weed control rated on indicated number of days post herbicide application | | | |
|---|---|---|---|---|---|---|---|---|
| (rate per acre) | 48 days | 83 days | 105 days | 118 days | 48 days | 83 days | 105 days | 118 days |
| 0.5 pints | 0 | 2 | 3 | 1 | 9 | 9 | 9 | 9 |
| 1 pint | 1 | 6 | 4 | 1 | 9 | 9 | 9 | 9 |
| 1 quart | 3 | 8 | 7 | 4 | 9 | 9 | 9 | 9 |

Production of Glyphosate-Tolerant Grasses

4RU and 5DU grasses can be grown under normal conditions for growing turf grasses, and bulk seed for large-scale planting can be obtained by methods known in certified seed production. For example, bulk seed may be produced by planting seeds of 5DU obtained from ATCC, allowing the mature plants to cross-pollinate with each other and then collecting the seed. Standard precautions should be taken to prevent cross-pollination from other grasses, such as growing the 5DU in an isolated plot of sterilized soil, removing adjacent vegetation, etc. The seeds of 4RU and 5DU deposited with ATCC are breeder seeds; propagation of plants from these seeds should preferably be performed only under the conditions specified in the 1998 Oregon Certified Seed Handbook, published by Oregon State University Extension Service, Corvallis, Oreg. 97331.

To confirm maintenance of the glyphosate-tolerance characteristic, a glyphosate herbicide (containing 41% w/v active ingredient glyphosate) may be applied to the plants at the equivalent of 1 pint per acre.

Exemplary Uses of Glyphosate Tolerant Grasses

4RU and 5DU may be used in the same way as other hard and tall fescue varieties, respectively. However, their resistance to glyphosate herbicides affords 4RU and 5DU particular advantages over other varieties. For example, with current commercially available varieties of fescue grasses, the preparation of a lawn that is to be made by seeding requires extensive preparation of the soil to remove weeds that may be present, often including soil fumigation. With 4RU and 5DU, such preparation may be avoided since most weeds that begin to grown in the new lawn may readily be removed by application of a glyphosate herbicide. With 4RU and 5DU, glyphosate herbicides may also be used to remove many of the most troublesome lawn weeds such as crabgrass (*Digitaria sanguinalis*), annual bluegrass (*Poa annua*), rat-tail fescue (*Vulpia myuros*) and annual ryegrass (*Lolium multiforum*).

Introducing Glyphosate Tolerance Into Other Grass Varieties

The glyphosate tolerance trait from 4RU and 5DU may be introduced into other grass varieties by conventional breeding techniques. For example, 4RU may be grown in pollination proximity to another variety of hard fescue grass, allowing cross pollination to occur between 4RU and the other variety, and then harvesting the hybrid seeds. Plants grown from these hybrid seeds are then tested for glyphosate tolerance by application of glyphosate herbicide at various levels. In this way, the glyphosate tolerance characteristic may be combined with other desirable plant characteristics. Thus, the provision of 4RU and 5DU enables the production of progeny plants of 4RU and 5DU having the glyphosate tolerance characteristic. "Progeny plants" of 4RU and 5DU are any plants that are the offspring of a cross between 4RU or 5DU and any other plant or plants. Preferably, such progeny plants retain the glyphosate tolerance characteristic of the 4RU or 5DU parent. In addition, 4RU and 5DU may be used as transformation targets for the production of transgenic grasses.

We claim:

1. A fescue grass plant having the morphological and physiological characteristics of plants grown from a *Festuca longifolia* (PST-4RU) grass seed deposited as ATCC 209893 or of plants grown from a *Festuca arundinacea* (PST-5DU) grass seed deposited as ATCC 209894.

2. Seed of a grass plant according to claim 1.

3. Progeny of a grass plant according to claim 1.

4. A fescue grass plant produced by crossing a grass plant according to claim 1.

5. Seed of a grass plant according to claim 3.

6. A method of producing grass seed, comprising
   (a) planting grass seed according to claim 1 under conditions that result in the germination of the seed, growth of grass plants and setting of progeny seed;
   (b) harvesting the progeny seed.

7. A method of producing a glyphosate-tolerant grass plant, the method comprising:
   (a) crossing a first grass plant with at least one other grass plant to produce progeny seed, wherein the first grass plant is a grass plant according to claim 1;
   (b) germinating the progeny seed to produce progeny grass plants; and
   (c) screening the progeny grass plants to select a progeny grass plant that is tolerant to glyphosate.

8. A glyphosate-tolerant grass plant produced by the method of claim 7.

9. A glyphosate-tolerant grass plant according to claim 8 wherein the grass plant is tolerant to application of at least 0.056 g per square meter of glyphosate.

10. A glyphosate-tolerant grass plant according to claim 8 wherein the grass plant is tolerant to application of at least 0.112 g per square meter of glyphosate.

11. *Festuca longifolia* (PST-4RU) grass seed deposited as ATCC 209893.

12. A grass plant produced by growing seed of claim 11.

13. *Festuca arundinacea* (PST-5DU) grass seed deposited as ATCC 209894.

14. A grass plant produced by growing seed of claim 13.

* * * * *